United States Patent [19]

Nankai et al.

[11] 4,431,507
[45] Feb. 14, 1984

[54] ENZYME ELECTRODE

[75] Inventors: Shiro Nankai, Yawata; Akihiro Imai, Ikoma; Takashi Iijima, Hirakata, all of Japan

[73] Assignee: Matsushita Electric Industrial Co., Ltd., Osaka, Japan

[21] Appl. No.: 338,957

[22] Filed: Jan. 12, 1982

[30] Foreign Application Priority Data

Jan. 14, 1981 [JP] Japan ..................... 56-4211

[51] Int. Cl.³ .................. G01N 27/54; C12Q 1/00; C12Q 1/54
[52] U.S. Cl. ..................... 204/403; 204/1 T; 435/817
[58] Field of Search ............. 204/195 B, 195 P, 1 E, 204/403; 435/817

[56] References Cited

U.S. PATENT DOCUMENTS 3,539,455 10/1970 Clark .
3,770,607 11/1973 Williams ................... 204/195 B
3,979,274 7/1976 Newman .
4,073,713 2/1978 Newman ................... 204/195 B
4,240,889 12/1980 Yoda .
4,356,074 10/1982 Johnson ................... 204/195 P

OTHER PUBLICATIONS

Guilbault, G. G., "Assay of Organic Species," *Ion Selective Electrode Reviews*, vol. 4, No. 2, 1982, pp. 212-215.

*Primary Examiner*—Howard S. Williams
*Assistant Examiner*—B. J. Boggs, Jr.
*Attorney, Agent, or Firm*—Wenderoth, Lind & Ponack

[57] ABSTRACT

The disclosure is directed to an improved enzyme electrode which includes a first electrode having at least one kind of an enzyme immobilized on it for electrochemically detecting a substance to be produced in association with a reaction based on the enzyme, and a second electrode for electrochemically removing materials which interfere with the detection by the first electrode. The second electrode is disposed at the side of a test solution containing a substrate of the enzyme with respect to the first electrode.

7 Claims, 5 Drawing Figures

Glucose concentration (mol/ℓ ×10⁻⁵)
Ascorbic acid concentration (mol/ℓ ×10⁻⁶)

( Magnification x 3000 )

ENZYME ELECTRODE

BACKGROUND OF THE INVENTION

The present invention generally relates to a polarographic cell and more particularly, to an enzyme electrode which is capable of quickly and readily measuring the substrate concentration of enzyme, and moreover, can be used repeatedly.

More specifically, the present invention relates to an enzyme electrode, which can remove influence of various interfering materials contained in a liquid to be tested or test solution (referred to as a test solution hereinbelow) which materials interfere with the electrochemical detection during measurement of the substrate concentration in the test solution by the use of a polarographic cell.

In one example for measuring the concentration of the substrate, which is a material subjected to the peculiar catalytic reaction of the enzyme, with the use of a polarographic cell, glucose is oxidized, through reaction of an oxide reductase enzyme such as glucose oxidase, to produce hydrogen peroxide $H_2O_2$ as shown in the following equations (1) and (2). Then, $H_2O_2$ thus produced is oxidized by the use of a platinum electrode or the like, and the concentration of the substrate (glucose) can be found from the oxidation current value obtained at this time.

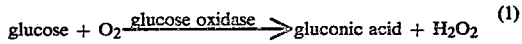

In order to form an enzyme electrode for measuring the concentration of a repeatedly usable substrate through application of this principle, in the above instance, for example, it is required to immobilize the water-soluble glucose oxidase on or in the vicinity of a current collector such as a platinum electrode or the like. For the immobilization of an enzyme, there have generally been employed various methods, for example, a method of using a high polymeric organic membrane such as cellulose or the like as an immobilizing carrier.

On the other hand, there is the problem of an interfering material contained in the test solution for the measurement of the substrate concentration by such an enzyme electrode. For example, during measurement of glucose in the blood, various coexisting materials such as uric acid, ascorbic acid, etc. contained therein are electrochemically oxidized directly on the electrode. Namely, since the coexisting materials are simultaneously oxidized in the oxidation of $H_2O_2$ on the electrode as shown in the equation (2), errors are undesirably involved in the current value to be obtained.

In order to overcome the disadvantage as described above, there has conventionally been proposed, for example, in U.S. Pat. No. 3,539,455, an enzyme electrode in which countermeasures are taken against the interfering materials referred to above. In this prior art, with employment of two platinum anodes, enzyme is immobilized only to one of the anodes, and by subtracting current values for the both, the influence of the interfering material is to be compensated. However, the above known method has a disadvantage in that it is very difficult to properly balance response characteristics of the two electrodes (platinum anodes).

In other prior arts proposed, for example, in U.S. Pat. Nos. 3,979,274 and 4,240,889, it is intended to prevent uric acid, ascorbic acid and the like from being diffused into the platinum electrode by disposing membranes of cellulose acetate, silicone rubber or the like at the side of the platinum anode contacting the test solution. The effect of the method described in the above prior arts with respect to the interfering materials depends upon selectivity of the membrane for $H_2O_2$ and the interfering material. Namely, the extremely fine membrane made of cellulose acetate or the like is set before the platinum electrode (on test solution side) for detecting $H_2O_2$ so as to select the interfering material such as ascorbic acid or the like from $H_2O_2$ by the use of this membrane. However, with the fine membranes in the prior arts as described above, diffusion of $H_2O_2$ is naturally restricted which reduces the sensitivity and response speed. Meanwhile, since the selectivity of these membranes is relative with respect to $H_2O_2$ and the interfering material, it is difficult to completely prevent such undesirable materials from interferring. It is considered that the effect becomes larger, with an increase of the membrane thickness to a certain extent, but a further reduction in the response-current (reduction in sensitivity) and response speed may result undesirably.

SUMMARY OF THE INVENTION

Accordingly, an essential object of the present invention is to provide an improved enzyme electrode which has an electrochemical activity with respect to a substrate to be subjected to the peculiar catalytic reaction of an enzyme, and is capable of quickly and readily measuring the concentration of the substrate, and moreover, may be used repeatedly.

Another important object of the present invention is to provide an improved enzyme electrode of the above described type which is simple in structure and stable in functioning at high reliability, and can be readily manufactured on a large scale at low cost.

In accomplishing these and other objects, according to one preferred embodiment of the present invention, there is provided an enzyme electrode which comprises a first electrode including at least one kind of an enzyme immobilized thereon for electrochemically detecting a substance to be produced in association with a reaction based on said enzyme, and a second electrode for electrochemically removing materials which interfere with the detection by said first electrode. The second electrode is disposed at the side of a test solution containing a substrate of the enzyme with respect to the first electrode.

By the arrangement according to the present invention as described above, an improved enzyme electrode has been advantageously presented, which substantial elimintes the drawbacks inherent in the conventional enzyme electrodes of this kind.

BRIEF DESCRIPTION OF THE DRAWINGS

These and other objects and features of the present invention will become apparent from the following description taken in conjunction with the preferred embodiment thereof with reference to the accompanying drawings, in which.

Before the description of the present invention proceeds, it is to be noted that like parts are designated by like reference numerals throughout several views of the accompanying drawings.

DETAILED DESCRIPTION OF THE INVENTION

Through various investigations and examinations carried out for the improvements of the disadvantages and drawbacks inherent in the conventional enzyme electrodes described earlier, the present inventors have come to provide an improved enzyme electrode having superior characteristics as described hereinbelow. The enzyme electrode of the present invention is composed of two electrodes, i.e. a first electrode and a second electrode.

More specifically, the first electrode is adapted to detect a material, for example, $H_2O_2$ to be produced in association with an enzyme reaction, while the second electrode is intended to electrochemically oxidize, in advance, interfering materials such as uric acid, ascorbic acid, etc., with respect to the first electrode. The enzyme electrode of the present invention is largely different from the conventional enzyme electrodes, in the following points. Namely, in the present invention, the interfering materials are not removed through physical or chemical selectivity of the membrane, but electrodes are employed to effect electrolytic oxidation so as to remove the interference in respect to $H_2O_2$ detection. Thus, a membrane as fine as that employed in the prior arts is not required in the arrangement of the present invention.

Figure 1:
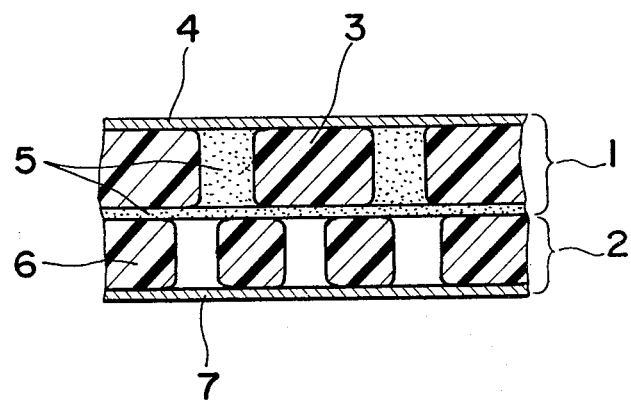
FIG. 1 is a schematic cross sectional view of an enzyme electrode according to one preferred embodiment of the present invention.
Figure 5:
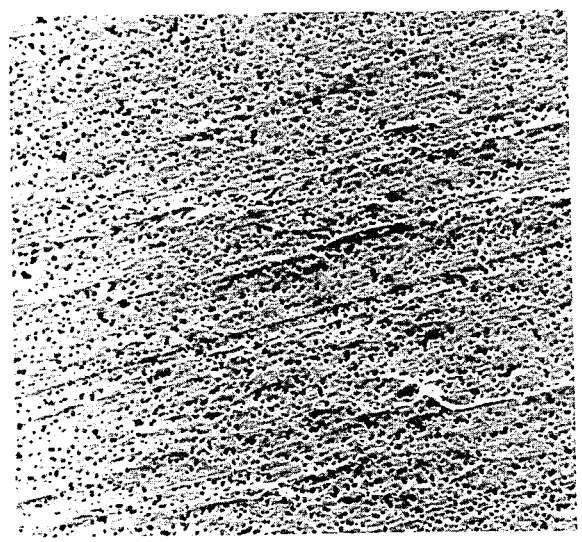
FIG. 5 is a photograph taken by a scanning type electron microscope at magnifications of 3000, and showing the structure on the surface of a polycarbonate porous membrane with a pore diameter of 2000 Å as a result of sputtering the membrane with platinum.

Referring now to the drawings, there is shown in FIG. 1 an improved enzyme electrode according to one preferred embodiment of the present invention. The enzyme electrode of FIG. 1 generally comprises a first electrode 1 which includes a porous membrane 3 for a carrier or support, a thin layer 4, for example, of platinum or the like formed on one surface of the porous membrane 3 by sputtering, deposition, etc., and an enzyme as an essential item immobilized on the other surface including the pores of the membrane 3 to form an enzyme immobilized layer 5 thereon, and a second electrode 2 which includes another porous membrane 6 also formed, on its one surface, with a thin layer 7 of platinum or the like formed in the similar manner as in the first electrode 1, with the first and second electrodes 1 and 2 being laminated at the intermediate enzyme immobilized layer 5 therebetween to constitute the enzyme electrode on the whole. In FIG. 5, there is shown a photograph of a surface structure of the enzyme electrode of FIG. 1 as observed by a scanning type electron microscope at magnifications of 3000.

It is to be noted here that, in the positional relation between both electrodes, the second electrode 2 is disposed to be at the side of the test solution with respect to the first electrode 1 so as to prevent the interfering materials contained in the test solution from being oxidized by the first electrode. When ascorbic acid is contained in the test solution in the measurement of a glucose concentration, by setting the potential of the second electrode at a sufficient oxidation potential of the ascorbic acid, electrolytic oxidation can be performed in advance. Since glucose is difficult to be directly electrolyzed, it reaches, as it is, the immobilized enzyme layer 5 (glucose oxidase in this case) of the first electrode so as to produce $H_2O_2$ through enzyme reaction. $H_2O_2$ thus formed is oxidized on the thin layer 4 of platinum and ultimately, a current is obtained, which depends only upon the glucose concentration in the test solution. As described so far, in the enzyme electrode of the present invention, materials for interfering with electrochemical detection are removed by electrochemical means, which arrangement produces excellent effects.

Figure 2:
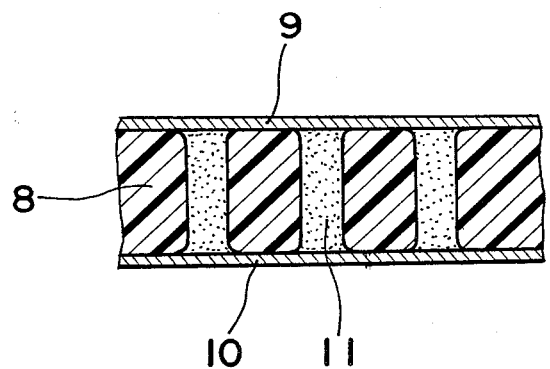
FIG. 2 is a view similar to FIG. 1, which particularly shows another embodiment of the present invention.

In another embodiment according to the present invention as shown in FIG. 2, the enzyme electrode includes one porous membrane 8 having a first electrode 9 of similar material as in the first embodiment formed at its one surface, and a second electrode 10 also of similar material formed at the other surface thereof, with an immobilized enzyme layer 11 being formed on the surface of the membrane 8 at the side of the first electrode 9 (not particularly shown) and also in the pores of said membrane 8.

By the arrangement in FIG. 2, there are such advantages that the enzyme electrode is simplified in its construction, while the response speeds, etc. thereof are further improved.

Furthermore, in the enzyme electrode according to the present invention, since the porous membrane is employed as a carrier for the electrode, with two electrodes being formed on the membrane so as to be of a thin membrane configuration on the whole, superior response speed and response sensitivity are available due to the fact that the response characteristics are hardly affected by expansion, tension variation or the like of the membrane during use, and a stable response results therefrom.

According to the present invention, the enzyme to be employed is not limited to one kind, but may be of a composite enzyme series. Similarly, for the immobilization of such enzymes, the arrangements are not restricted to those as in the embodiments of FIGS. 1 and 2, but may further be modified in various ways, for example, in such a manner that enzyme is preliminarily immobilized on a proper carrier for being laminated as in a sandwich with the second electrode so as to be located in the vicinity of the first electrode. Meanwhile, for forming the first and second electrodes, any materials, for example, metals such as platinum, gold, etc., or metallic oxides such as ruthenium oxides and the like may be employed so long as they meet the requirements as described earlier.

Hereinbelow, EXAMPLES are inserted for the purpose of illustrating the present invention, without any intention of limiting the scope thereof.

EXAMPLE 1

A porous polycarbonate membrane of 2000 Å in pore diameter, 10 μm in membrane thickness, and $3 \times 10^8$ pores/cm$^2$ in pore density, was used as a carrier for the first electrode. A layer of platinum of 10 through 20 Ω in surface resistance was formed through sputtering on one surface of the membrane. Subsequently, a glucose oxidase aqueous solution (100 mg/ml) was spread at a rate of 10 μl/cm² on the surface of the membrane at its side opposite to the platinum layer. After drying, an immobilizing reaction was effected for one hour at 25° C. in glutaraldehyde vapor, with subsequent washing with water.

Meanwhile, another porous polycarbonate membrane of 8000 Å in pore diameter, 10 μm in membrane thickness, 3×10⁷ pores/cm² in pore density, was employed as a carrier for the second electrode, and a layer of platinum was formed on one surface of the membrane in the similar manner as above to form the second electrode. The two electrodes thus obtained were caused to adhere to each other through depression by laminating them so that the respective platinum layers may be located on external sides, and thus, the enzyme electrode in a thin membrane shape on the whole was obtained.

Figure 3:
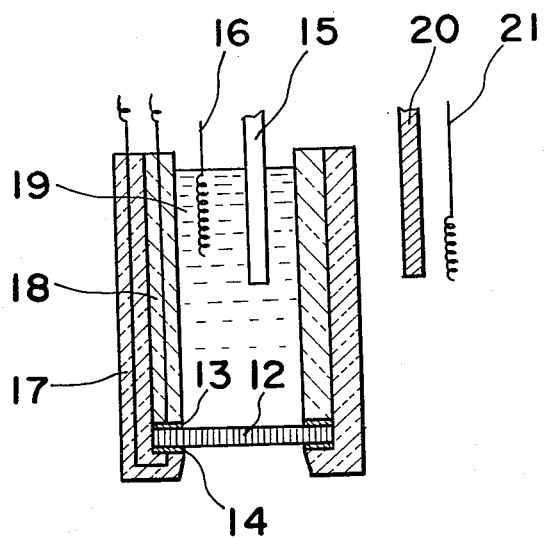
FIG. 3 is a schematic side sectional view of an electrode holder in which the enzyme electrode according to the present invention is mounted.

In FIG. 3 schematically showing a cross section of a cylindrical electrode holder equipped with the enzyme electrode of the present invention as described so far, and an electrode system employed therefor, the enzyme electrode 12 is mounted in a main body 18 of the electrode holder through an outer tube 17 in such a manner that the platinum layer of the first electrode is directed towards the inner side of the electrode holder in which a phosphate buffer solution 19 is accommodated, with the platinum layer of the first electrode contacting a platinum lead 13, and that of the second electrode contacting another platinum lead 14 respectively as shown. Additionally, a reference electrode 15 of Ag/AgCl and a counter-electrode 16 for the first electrode are provided in the interior of the electrode holder, while another reference electrode 20 of Ag/AgCl and a counter-electrode 21 for the second electrode are disposed outside the electrode container to constitute the electrode system, with the interior of the electrode holder being filled with the phosphate buffer solution 19 at a pH 5.6 as ilustrated.

With the electrodes as described above immersed in the phosphate buffer solution 19 at a pH 5.6, current variations following variations in the concentration were measured through addition thereto of glucose or ascorbic acid.

Figure 4:
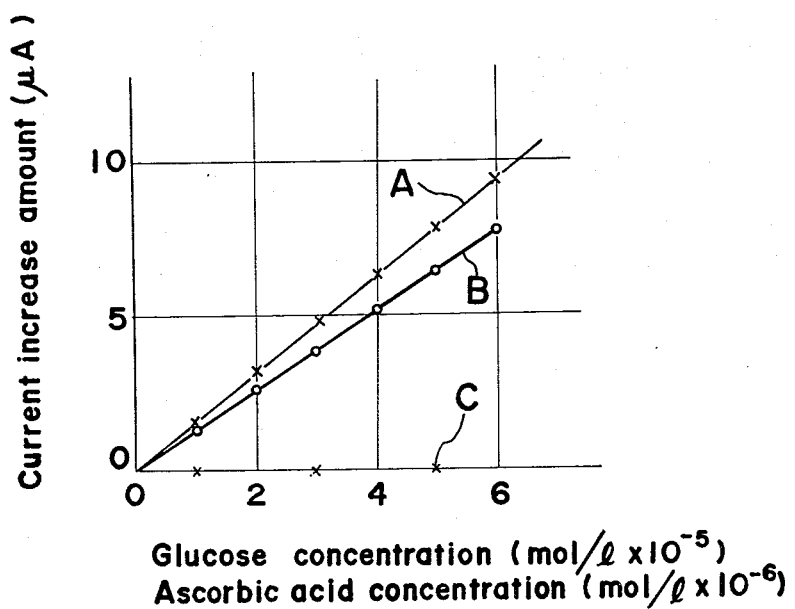
FIG. 4 is a graph showing the relation between concentration and current increase amount with respect to glucose and ascorbic acid.

In FIG. 4, there is shown a graph representing the amount of current increase with respect to the first electrode. In the graph of FIG. 4, a line A relates to ascorbic acid, in the case where the potential for the first electrode is set at +0.60 V (VS.Ag/AgCl), with no potential applied to the second electrode at all. Meanwhile, the current increase with respect to glucose under the same conditions as above is represented by a line B. The response with glucose was quick, with the current rapidly increased with the addition of glucose, and a steady value was reached after 15 through 20 seconds, while, current increase of approximately 4 μA with respect to 3×10⁻⁵ mole/l was observed. The current increase with respect to the ascorbic acid in a case where the first electrode and the second electrode were both set to +0.60 V (VS.AG/AgCl) was not observed at all as shown at C so as to be in agreement with B with respect to glucose under the same conditions, without any influence at all on the measurement of glucose.

According to the response characteristics of the enzyme electrode disclosed in U.S. Pat. No. 4,224,125 assigned to the same assignee as the present application, it took about two minutes to achieve steady current after addition of glucose. Meanwhile, the current increase was approximately 25 μA with respect to 3×10⁻³ mole/l. In other words, in the enzyme electrode of the present application, the performance six to eight times in response speed, and sixteen times in sensitivity was achieved, without influences by the interfering materials.

EXAMPLE 2

The first electrode was prepared in the similar manner as in EXAMPLE 1, while a porous polycarbonate membrane of 3.0μ in pore diameter, 10 μm in membrane thickness, and 2×10⁶ pores/cm² in pore density was employed for a carrier of the second electrode. A platinum layer was formed by sputtering on each side of the above membrane to provide resistance of 2 through 4Ω therebetween, with the platinum layer being sufficiently penetrated uniformly into the pores also.

The electrode thus prepared was mounted in the electrode holder in the similar manner as in EXAMPLE 1 for measurements. The enzyme electrode showed a similar favorable response as described hereinabove, with respect to glucose. Moreover, no influence was observed at all with respect to ascorbic acid even at the concentration of 2×10⁻² mole/l. This is attributable to the fact that the second electrode electrolytically oxidizes ascorbic acid sufficiently.

EXAMPLE 3

A porous polycarbonate membrane of 2000 Å in pore diameter, 10 μm in membrane thickness and 3×10⁸ pores/cm² in pore density was employed as a carrier, while a platinum layer was formed, by sputtering, on its each side. The resistance values thereof were 10 through 20Ω on each side, and 10 MΩ or more between the both sides. In other words, the opposite surfaces of one porous membrane were, respectively, made the first electrode and the second electrode as shown in FIG. 2. The glucose oxidase aqueous solution (100 mg/ml) was spread only on one side of the membrane (the side of the first electrode) for immobilization as described earlier. In this case, although the immobilization was effected even over the platinum layer of the first electrode, there were no problems in measurements. Upon measurements of the response characteristics of the enzyme electrode thus obtained in the similar manner as in EXAMPLE 1, a steady current was obtained after about seven seconds with respect to glucose, with sensitivity about twice as large. Meanwhile, adverse effect could be removed with respect to ascorbic acid as in EXAMPLE 1.

As is clear from the foregoing description, by electrolytically oxidizing ascorbic acid in advance by the use of the second electrode, the interruption to the first electrode may be eliminated. The large effect for the electrolytic oxidation as described above, is considered to be attributable to the fact the thin porous membrane is employed as the second electrode, with the platinum thin layers being formed on the membrane surfaces and, furthermore, into the pores so as to form the enzyme electrode in the porous thin membrane shape on the whole. Moreover, by laminating the second electrode and first electrode as described above in the form of a thin membrane through close adhesion, an improved enzyme electrode, superior in response speed and response sensitivity has been advantageously presented.

It should be noted here that, in the foregoing embodiments, although the enzyme electrode of the invention was mainly described with reference to the case where glucose oxidase was employed as the enzyme, the present invention is not limited in its application to such an arrangement alone, but may similarly be applied to the cases where $H_2O_2$ is produced in the enzyme reaction, and also, where a plurality of enzyme reactions are related thereto.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as included therein.

What is claimed is:

1. An enzyme electrode assembly which comprises a first electrode including at least one enzyme immobilized thereon for electrochemically detecting a substance to be produced in association with a reaction based on said enzyme, and a second electrode for electrochemically removing materials which interfere with said detection by said first electrode, said second electrode being disposed at the side of a test solution containing a substrate of said enzyme with respect to said first electrode.

2. An enzyme electrode assembly as claimed in claim 1, wherein said second electrode is mode of a thin layer formed selectively of a metal or metal oxide on a porous membrane.

3. An enzyme electrode assembly as claimed in claim 1 or 2, wherein said first electrode is made of by a porous membrane having a thin layer of a metal or metal oxide formed on its surface, with the enzyme being immobilized on said porous membrane.

4. An enzyme electrode assembly as claimed in claim 3, wherein said first electrode and second electrode are laminated one upon another.

5. An enzyme electrode assembly as claimed in claim 3, wherein said first electrode is formed at one side of the porous membrane, with said second electrode being formed at the other side of said porous membrane.

6. An electrode assembly comprising a first electrode including at least one enzyme immobilized thereon for electrochemically detecting a substance to be produced in association with a reaction based on said enzyme, said enzyme electrode being made of a porous membrane having a thin layer of a metal or metal oxide layer on one surface and at least one enzyme immobilized on its opposite surface and a second electrode for electrochemically removing materials which interfere with said detection by said first electrode, said second electrode being also composed of a porous membrane with a thin layer of a metal or metal oxide on one side of the porous membrane;

said first and second electrodes being laminated such that the immobilized enzyme(s) is sandwiched between between the two porous membranes and the metal or metal oxide layers are located on the outer portions of the laminated structure.

7. An electrode assembly comprising a porous membrane having first a metal or metal oxide electrode layer located on one side with an enzyme immobilized on said layer and within the pores of the membrane to constitute a first electrode and a second electrode metal and metal oxide layer located in the opposite side of the porous membrane, said first electrode-functioning to detect a substance to be produced in association with an enzyme reaction, based on said enzyme and said second electrode functioning to electrochemically remove materials which interfere with said detection by the first electrode.

* * * * *